United States Patent [19]

Stenglein et al.

[11] Patent Number: 5,221,611
[45] Date of Patent: Jun. 22, 1993

[54] DDI IMMUNOASSAYS, DERIVATIVES, CONJUGATES AND ANTIBODIES

[75] Inventors: Kenneth J. Stenglein, St. Louis; Dennis M. Murray, Eureka, both of Mo.

[73] Assignee: Sigma Chemical Company, St. Louis, Mo.

[21] Appl. No.: 717,614

[22] Filed: Jun. 19, 1991

[51] Int. Cl.$^5$ .................. C07H 19/16; G01N 33/532; G01N 33/577; C12P 21/08

[52] U.S. Cl. ..................... 435/7.1; 435/7.9; 435/28; 435/172.2; 435/195; 435/240.27; 436/94; 436/544; 436/547; 530/388.21; 530/402; 530/362; 530/27.14

[58] Field of Search ............... 435/7.1, 7.9, 28, 172.2; 436/94, 501, 544, 545, 546, 547, 548; 530/387, 402, 388.21; 536/26

[56] References Cited

U.S. PATENT DOCUMENTS

| | | | |
|---|---|---|---|
| 4,835,104 | 5/1989 | Yokozeki et al. | 435/87 |
| 4,861,759 | 8/1989 | Mitsuya et al. | 514/46 |
| 4,880,782 | 11/1989 | Eckstein et al. | 514/45 |
| 4,920,210 | 4/1990 | Koszalka et al. | 536/24 |
| 4,962,193 | 10/1990 | Yokozeki et al. | 536/24 |
| 4,970,148 | 11/1990 | Yokozeki et al. | 435/88 |
| 5,002,868 | 3/1991 | Jacobson et al. | 435/6 |
| 5,051,361 | 9/1991 | Stenglein et al. | 435/7.9 |

FOREIGN PATENT DOCUMENTS

| | | |
|---|---|---|
| 1269044 | 5/1990 | Canada . |
| 0251786 | 1/1988 | European Pat. Off. . |
| 0398230 | 11/1990 | European Pat. Off. . |

OTHER PUBLICATIONS

Ray et al, Drug Metab. Dispos. 18:654-8, 1990, as abstracted in Chemical Abstracts 114:146z, p. 12, 1991.
Zubay, Biochemistry, pp. 877 and 952-954, 1983.
Agarwal et al., Aids Research and Human Retroviruses: 5: pp. 541-550, 1989.
Al-Deen et al., J. of Chromatography 512: 409-414, 1990.
MacPherson, pp. 77-90 in Radionuclides in Clinical Chemistry, Howard et al, editors, 1980.
O'Sullivan, pp. 37-69 in Practical Immunoassay, Butt, editor, 1984.
Yalow et al., pp. 1-21, in Principles of Competitive Protein-Binding Assays, Odell, editor, 1971.
R. Webb II, et al., "Synthesis of 2',3'-dideoxyinosine", Nucleosides and Nucleotides, vol. 7, No. 2, 1988, pp. 147-153.
J. Montgomery et al., "Further Studies on the Alkylation of Purines", Montgomery, Hewson, Clayton, and Thomas, Journal of Organic Chemistry, vol. 31, 1966, pp. 2202-2210.
J. H. Hoofnagle et al. "Method of Treatment of Hepatitis", Report No. 7-351502, Filed May 15, 1989, US Patent Application.
E. DeClercq, "Chemotherapeutic Approaches to the Treatment of the Acquired Immune Deficiency Syndrome (AIDS)" Journal of Medicinal Chemistry, vol. 29, No. 9, 1986, pp. 1560-1569.
M. Johnson et al., "Phosphorylation of 2',3'-Dideoxyinosine by Cytosolic 5'-Nucleotidase of Human Lymphoid Cells", Molecular Pharmacology, vol. 36, 1989, pp. 291-295.
N. Hartman et al., "Pharmacokinetics of 2',3'-dideoxyadenosine and 2',3'-dideoxyinosine in patients with severe human immunodeficiency virus infection", Clinical Pharmacology and Therapeutics, vol. 47, 1990, pp. 647-654.

(List continued on next page.)

Primary Examiner—Robert A. Wax
Assistant Examiner—Stephen Walsh
Attorney, Agent, or Firm—Senniger, Powers, Leavitt & Roedel

[57] ABSTRACT

This invention relates to a method for the immunoassay of ddI (2',3'-dideoxyinosine), also known as didanosine, in biological fluids such as serum, semen, plasma and urine, as well as other body fluids. The invention also includes (1) various novel analogs of ddI useful in preparing immunogens for antibodies to ddI and in preparing labeled ddI, (2) immunogens for antibodies to ddI, (3) antibodies to ddI, (4) labeled ddI analogs and (5) diagnostic test kits for the immunoassay.

48 Claims, No Drawings

OTHER PUBLICATIONS

R. Dolin et al., "2',3'-Dideoxyinosine in Patients with AIDS AIDS-Related Complex", Reviews of Infectious Diseases, vol. 12, Supplement 5, 1990, pp. 540–551.

J. Layayre et al., "On the Conformation of Some Substituted Adenosine 5'-Monophosphates", Biochemical and Biophysical Research Comm. vol. 65, No. 4, 1975, pp. 1355–1362.

R. Yarchoan et al., "In Vivo Activity Against HIV and Favorable Toxicity Profile of 2',3'-Dideoxyinosine", Science vol. 245, 1989, 412–415.

J. Kelley, "The Analytical Chemistry of anti-AIDS agents", File 266: Federal Research in Progress, 1987.

S. El Dareer, "Disposition of 2',3'-dideoxyadenosine and 2',3'-dideoxyinosine in mice", Investigational New Drugs, vol. 7, 1989, pp. 139–146.

J. Kalin et al., "Determination of 2'3'-dideoxyadenosine, 2'3'-dideoxyinosine and 2',3'-dideoxycytidine in biological samples", Journal of Chromatography, vol. 431, 1988, pp. 184–191.

J. Russell et al., "Comparative Pharmacokinetics of New Anti-HIV Agents: 2',3'-Dideoxyadenosine and 2',3'-Dideoxyinosine" Biochemical Pharmacology, vol. 38, No. 9, 1989, pp. 1385–1388.

M. Carpen et al. "High-performance liquid chromatographic method for analysis of 2',3'-dideoxyinosine in human body fluids", Journal of Chromatography, vol. 526, 1990 pp. 69–75.

S. Kaul et al., "Pharmacokinetics of 2',3'-Dideoxyinosine (BMY-40900), a New Anti-Human Immunodeficiency Virus Agent, after Administration of Single Intravenous Doses to Beagle Dogs", Antimicrobial Agents and Chemotherapy, vol. 35, No. 4, 1991 pp. 610–614.

H. Mitsuya et al., "Inhibition of the in vitro infectivity and cytopathic effect of human T-lymphotrophic virus type III/lymphadenopathy-associated virus (HTLV-III/LAV) by 2',3'-dideoxynucleosides" Proc. Natl. Acad. Sci. USA, vol. 83, 1986 pp. 1911–1915.

B. Anderson et al., "Uptake Kinetics of 2',3'-Dideoxyinosine into Brain and Cerebrospinal Fluid of Rats: Intravenous Infusion Studies", The Journal of Pharmacology and Experimental Therapeutics, vol. 253, No. 1, 1990, pp. 113–118.

H. Nakashima et al., "Tetrazolium-based plaque assay for HIV-1 and HIV-2, and its use in the evaluation of antiviral compounds", Journal of Virological Methods, vol. 26, 1989 319–330.

DDI IMMUNOASSAYS, DERIVATIVES, CONJUGATES AND ANTIBODIES

This invention relates to a method for the immunoassay of ddI (2',3'-dideoxyinosine), also known as didanosine, in biological fluids such as serum, semen, plasma and urine, as well as other body fluids. The invention also includes (1) various novel analogs of ddI useful in preparing immunogens for the production of antibodies to ddI and in preparing labeled ddI, (2) immunogens for the production of antibodies to ddI, (3) antibodies to ddI, (4) labeled ddI analogs and (5) diagnostic test kits for the immunoassay.

BACKGROUND OF THE INVENTION

Competitive binding immunoassays for quantitatively measuring the presence of physiologically active compounds (ligands) are based on the competition between a ligand in a test sample and a labeled reagent, referred to as a tracer, for a limited number of binding sites on antibodies or receptors specific to the ligand and the tracer. The concentration of ligand in a sample to be assayed determines the amount of tracer or label that will specifically bind to an antibody. By measuring the amount of tracer-antibody complex a quantitative determination of the amount of ligand in the test sample is provided. When necessary, modification of such ligand to prepare an immunogen should take into account the effect on the structural specificity of the antibody. That is, in choosing a site on a ligand for conjugation to a carrier such as protein, the selected site is chosen so that administration of the resulting immunogen will provide antibodies which will recognize the original ligand. Furthermore, not only must the antibody recognize the original ligand, but significant characteristics of the ligand portion of the immunogen must remain so that the antibody produced after administration of the immunogen may distinguish compounds closely related to the ligand from other compounds which may also be present in the patient sample. In addition, the antibodies should have high binding constants.

Also, the tracer must effectively compete with the ligand for antibody binding in a reproducible manner and provide for significant changes in the measured signal with small changes in the concentration of the ligand over the concentration range of interest.

Other considerations for an immunoassay method are that it is not affected by materials present in the sample to be assayed, an easily determinable signal is obtained, the tracer, standards and antibodies have good storage life and are stable under the assay conditions. Also, the tracer and standards must be readily recognizable by the antibodies for the ligand.

ddI (2',3'-dideoxyinosine), which can be represented by the formula:

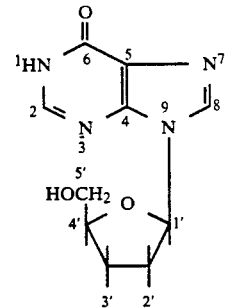

has been shown to be an effective drug in the treatment of Acquired Immunodeficiency Syndrome (AIDS). As with any drug, and especially one having serious side effects at high dosage levels, such as ddI, the formal establishment of a therapeutic range for a patient being treated with the drug is necessary. The recognized method for measuring ddI plasma levels employs high performance liquid chromatography (HPLC) which is a sensitive and reasonably precise technique. However, although HPLC can be used for measuring ddI concentrations in noninfective samples and in HIV-positive samples, the HPLC method is not practical for the routine monitoring of ddI in HIV-positive samples due to the disadvantages of a long analysis time, elaborate sample preparation requirements, including complicated solid phase extraction, a relatively large sample size (250 $\mu$l–3,000 $\mu$l) and interference by body fluid components in the sample. A particular problem in using HPLC to monitor ddI levels in pediatric patients is the difficulty in obtaining samples of sufficient volume. Also, HPLC is subject to interference from endogenous compounds.

The development of an analytical method for measuring ddI levels in a patient being treated with ddI which could minimize sample manipulation, employ disposable equipment as much as possible, reduce the sample size needed and shorten the length of the assay time is therefore needed. It is preferred that such a method not be subject to interference from endogenous compounds, or hemolysis or typically prescribed drugs.

SUMMARY OF THE INVENTION

Immunoassays provide a useful method for quantitatively determining drug levels in small samples (1–250 $\mu$l), have a rapid turn-around time, are easy to perform and can be automated for processing large numbers of samples. Immunoassays are therefore suitable for measuring levels of drugs in patients and are especially useful where sample handling must be minimized.

It is therefore an object of this invention to provide an assay for the determination of ddI (2',3'-dideoxyinosine) levels in a sample which meets the needs described above, especially in the establishment of a formal therapeutic range in a patient undergoing treatment with ddI. More specifically it is an object of this invention to provide an immunoassay for determining the presence or amount of ddI in a sample. The immunoassay comprises intermixing with said sample a labeled analog of ddI (tracer) or biologically acceptable salt thereof, and an antibody capable of specifically recognizing said ligand and said tracer, and then determining the amount of tracer bound to antibody by a suitable technique.

A further object is to provide a competitive binding assay having many advantages over an HPLC assay, including the requirement of a smaller sample size, allowing for its use with pediatric patients, decreased assay time, simple extraction procedures if required and a lack of interference from endogenous components or cross-reactivity with other drugs or drug metabolites. It is recognized that noncompetitive immunoassays are possible and is contemplated that the ddI antibodies within the scope of the invention would be useful for the determination of ddI concentration using such immunoassays. Further, the application of such ddI antibodies to such immunoassays is within the skill of the art.

A still further object is to provide various novel materials useful in carrying out the method of this invention or for the preparation of such materials including (1) analogs of ddI which are suitable for preparing immunogens for ddI by coupling to a carrier, such as protein, or, are suitable for preparing labeled ddI derivatives (tracers) by coupling to indicator moieties, such as fluorescein; (2) immunogens suitable for the preparation of monoclonal or polyclonal antibodies to ddI; (3) antibodies obtained from the immunization of suitable animal species with such immunogens; and (4) labeled ddI derivatives suitable for use in the method of this invention.

In addition, an object of the invention is to provide a diagnostic kit useful in the practice of the immunoassays of the invention.

It is also contemplated that compounds similar in structure to ddI will be developed for the treatment of AIDS, and a further object of this invention therefore is to provide an assay for those ddI related compounds to the extent that such compounds are recognized by antibodies to ddI.

These and other objects will become apparent from the detailed description of the invention.

DETAILED DESCRIPTION OF THE INVENTION

For any immunoassay method there are three essential ingredients: a tracer, an antibody, and the sample to be analyzed. Of course standards, containing known amounts of ligand, are also necessary in order to provide a basis for the determination of the ligand level in the sample to be analyzed.

Controls may also be utilized to verify the accuracy of the analysis.

ddI Immunoassay

In accordance with the method of this invention, a sample containing or suspected of containing ddI is intermixed with a tracer or a biologically acceptable salt thereof and an antibody specific to ddI and the tracer. ddI present in the sample and the tracer compete for a limited number of antibody binding sites resulting in the formation of ddI-antibody and tracer-antibody complexes. By maintaining the concentration of tracer and antibody constant, the amount of tracer-antibody complex formed is inversely proportional to the amount of ddI present (as ddI-antibody complex) in the sample. By determining the amount of tracer-antibody complex in the reaction mixture a quantitative determination of the amount of ddI in the sample is made.

The concentration of ddI in the sample assayed will vary depending on the establishment of a therapeutic dosage based upon, for example, the body fluid measured and dose given. The sensitivity of the assay may be optimized accordingly. High concentrations of ddI may be assayed by dilution of the original sample.

In addition to the concentration range of ddI, considerations such as whether the assay is qualitative, semi-quantitative or quantitative, the equipment employed, and the characteristics of the tracer and antibody will normally determine the concentration of the tracer and antibody to be employed. While the concentration of ddI in the sample will normally determine the range of concentration of the tracer and the antibody, in order to optimize the sensitivity of the assay, individual concentrations of tracer and antibody will be determined empirically. The latter concentrations can be readily ascertained by those skilled in the art. Other considerations involved in optimizing a particular immunoassay include pH and assay temperature.

The pH at which the method of the present invention is practiced should be controlled in those assays where pH is important, for example assays using a fluorescein derivative. Various buffers may be employed in order to achieve and maintain the desired pH during the assay procedure. Representative buffers include borate, phosphate, carbonate, tris(hydroxymethyl)aminomethane (Tris), barbital, and the like. The particular buffer selected is not critical for the present invention, but in an individual assay, a specific buffer may be preferred in view of the method chosen and the components employed. The cation portion of the buffer will generally determine the cation portion of the tracer salt in solution.

The methods of the present invention are practiced at moderate temperatures and preferably at a constant temperature. The temperature will normally range from about 0° C. to about 50° C., more typically from about 15° C. to about 40° C.

The invention is not limited to a particular assay procedure, and therefore encompasses both homogeneous and heterogeneous procedures, including procedures such as fluorescence polarization immunoassay (FPIA), fluorescence immunoassay (FIA), enzyme immunoassay (EIA), nephelometric inhibition immunoassay (NIA), and radioimmunoassay (RIA). The indicator moiety is selected so as to meet the needs of various users of the method which are often dictated by the availability of assay equipment and compatible immunoassay procedures.

Homogeneous immunoassays are assays that do not require the separation of antibody bound tracer from free tracer. The antigen-antibody interaction causes, directly or indirectly, a measurable change in the signal.

The preferred homogeneous assays are those utilizing an enzyme or a fluorescent reagent, because they are nonisotopic, resulting in fewer waste disposal problems. Enzyme immunoassays also are preferred because they are quite sensitive and are therefore capable of measuring a lower ddI concentration. Both of these types of assays are also precise and easily automated, the assays are simple, the sample size per assay is relatively small, and assay results compare well with results obtained from an HPLC assay.

A preferred homogeneous immunoassay is a fluorescence polarization immunoassay (FPIA). For example, one can use fluorescein labeled ddI as the tracer. Briefly, fluorescein labeled ddI and unlabeled ddI present in the sample to be analyzed compete for a limited number of antibody combining sites. Increasing amounts of unlabeled ddI present in a given sample leads to a corresponding decrease in the amount of antibody bound fluorescein labeled ddI and causes a decrease in the polarization of the sample. The extent of polarization is therefore inversely proportional to the ddI concentration in the sample. See for example, Dandliker, W. B. and de Saussure, V. A., *Immunochemistry*, 7, 799 (1970).

A protein precipitating reagent may be necessary in fluorescence immunoassays including fluorescence polarization immunoassays. The precipitating reagent is used to gain sensitivity by reducing nonspecific background fluorescence and scattering of light due to various materials present such as serum proteins and bilirubin-albumin complexes. The present invention includes the addition, to the sample to be analyzed, of a precipitating reagent such as acetonitrile; ammonium sulfate; sodium sulfate; trichloroacetic acid, with or without methanol; sulfosalicylic acid, with methanol, or dioxane or N,N-dimethylacetamide; polyvinyl sulfonic acid with or without methanol as well as with sulfuric acid or phosphoric acid, and chromotropic acid with methanol. After precipitation of a portion of the interfering compounds and their separation, the pH of the serum extract (supernatant) should be adjusted by using a buffer with sufficient buffering capacity to permit the ligand-antibody interaction to occur under favorable conditions. Examples of such buffers are: glycine; phosphate; borate; carbonate; Tris; ethanolamine; triethanolamine; diethanolamine; piperazine; tricine; and ammonia. In the present invention, the preferred buffer is a phosphate solution. Sample preparation methods that are alternatives to protein precipitation include chromatography and solid phase extraction.

Substrate-labeled fluorescent immunoassay is another homogeneous immunoassay in which an enzyme, such as β-galactosidase, hydrolyses a non-fluorescent conjugate of ddI, such as ddI-umbelliferone-β-galactoside, producing a fluorescent product which can be measured in a spectrofluorometer. Since the antibody to ddI will bind to the non-fluorescent ddI conjugate and interfere with the conversion of the conjugate to the fluorescent product, the addition of ddI creates a competition for ddI antibody combining sites. Thus, the concentration of fluorescent product is proportional to the concentration of ddI.

Fluorescence quenching and fluorescence enhancement immunoassays are other homogeneous fluorescent assays based on the observation that some antibodies, upon binding to a fluorescent molecule, cause either an enhancement or decrease in fluorescence. For example, ddI can be conjugated to a fluorescent molecule which, upon binding to selected ddI antibodies, can quench the fluorescence of the fluorescent ddI conjugate. ddI can compete with the fluorescent ddI conjugate for a limited number of ddI antibody combining sites and reduce the amount of quenching. Therefore, the fluorescence intensity of the assay is proportional to the ddI concentration.

A homogeneous immunoassay using phosphorescence quenching of erythrosin can be performed in a manner similar to that used in fluorescence quenching.

Enzyme immunoassays (EIA) are a broad class of immunoassays based upon the determination of enzyme activity as a measure of the antigen antibody interaction. Homogeneous enzyme immunoassays are assays that do not require the separation of the bound tracer from free tracer, but rely on modulation of enzyme activity by the specific interaction of antigen with antibody.

For example, ddI can be conjugated near the active site of an enzyme such as glucose-6-phosphate dehydrogenase. Upon the addition of antibodies to ddI, the subsequent enzyme activity is reduced by steric interference of the antibody with the enzyme substrate. The addition of ddI competes with the ddI-enzyme conjugate for a limited number of antibody combining sites, thus preventing interference by antibodies to ddI with enzyme activity. The enzyme activity is directly proportional to the ddI in the sample.

Cofactor-labeled antigen EIA is yet another type of homogeneous enzyme immunoassay that can be performed by conjugating ddI to a cofactor. One such cofactor is nicotinamide-6-(2-amino-ethylamino)adenine dinucleotide (aeaNAD+). The addition of antibodies to ddI binds the ddI-aeaNAD+ conjugate and inhibits the activity of an NAD dependent enzyme, such as lactate dehydrogenase. ddI will compete with ddI-aeaNAD+ for a limited number of ddI antibody combining sites. As a result a change in absorbance of the reaction mixture will be proportional to the ddI concentration.

An additional type of homogeneous immunoassay is an agglutination immunoassay (AIA). For example, latex particles can be coated with a multivalent ddI conjugate (prepared by conjugating ddI analogs to a carrier) and will agglutinate (clump) upon addition of antibodies to ddI. The addition of ddI will cause competition for the limited number of antibody combining sites and cause a decrease in the turbidity of the mixture. Erythrocytes have also been used as indicator particles in place of latex particles.

A nephelometric inhibition immunoassay (NIA) is another type of homogeneous immunoassay that utilizes a multivalent ddI conjugate. Typically this conjugate is prepared from a high molecular weight carrier such as horse apoferritin or serum proteins. Upon addition of antibody to ddI, the multivalent ddI conjugate forms complexes with the antibody to ddI, thus increasing the amount light scatter in the reaction mixture. The addition of ddI decreases the size of the complexes formed by multivalent ddI conjugates and antibodies to ddI, by competing with the multivalent ddI conjugate for a limited number of antibody combining sites.

A sol particle immunoassay (SPIA) utilizes inorganic colloidal particles as the indicator. While SPIA can be performed as a heterogeneous immunoassay, it can also be structured as a homogeneous immunoassay. For example, in a gold SPIA antibodies to ddI can be adsorbed to gold particles. The addition of multivalent ddI conjugates causes the gold-antibody to ddI complexes to agglutinate causing a change in the absorption spectrum of the gold particles, i.e., the color changes from red to blue. ddI will compete with the multivalent ddI conjugates, decreasing the color change.

Heterogeneous immunoassays are assays that require the separation of bound tracer from free tracer prior to determining the amount of ligand in the sample. While homogeneous immunoassays are most preferred because they do not require the additional separation step of heterogeneous immunoassays, among heterogeneous immunoassays those with a radioactive or enzyme group as the indicator group are preferred. This is because, like homogeneous EIAs, radioactive or enzymatic heterogeneous immunoassays are precise, easily automated, utilize a small sample size and can be more sensitive than FPIAs.

Radioimmunoassays (RIA) are heterogeneous immunoassays utilizing radioactively labeled ligands. For example, ddI can be directly labeled with $^3$H or a ddI analog can be labeled with $^{125}$I. Labeled ddI competes with unlabeled ddI for a limited number of antibody combining sites. After the bound complex of labeled ddI-antibody to ddI is separated from the unbound (free) labeled ddI, the radioactivity in the bound fraction, or free fraction or both is determined in an appropriate radiation counter. The concentration of bound labeled ddI is inversely proportional to the concentration of unlabeled ddI. The antibody to ddI can be in solution with separation of free and bound ddI being accomplished using charcoal or a second antibody specific for the animal species whose immunoglobulin contains the antibody to ddI. Alternatively, antibody to ddI can be attached to the surface of an insoluble material. In this case, separation of bound and free ddI is performed by appropriate washing.

Immunoradiometric assays (IRMA) generally refer to heterogeneous immunoassays in which the antibody reagent is radioactive labeled (the tracer). An IRMA requires the production of a multivalent ddI conjugate, as for example by conjugation to a protein such as rabbit serum albumin. The multivalent ddI conjugate must have at least 2 ddI residues per molecule and the ddI residues must be of sufficient distance apart to prevent steric interference of binding by at least two antibodies to ddI. For example, in an IRMA the multivalent ddI conjugate can be attached to a solid surface such as a plastic sphere. Unlabeled ddI and antibody to ddI which is radioactive labeled are added to a test tube containing the multivalent ddI conjugate coated sphere. The ddI competes with the multivalent ddI conjugate for ddI antibody binding sites. After an appropriate time, the unbound reactants are removed by washing and the amount of radioactivity on the solid phase is determined. The radioactivity bound is inversely proportional to the concentration of ddI.

Alternatively, antibody to ddI can be used to coat a plastic sphere. The addition of the multivalent ddI conjugate and ddI results in a competition for binding sites on the solid phase antibody sphere. After an appropriate incubation, the sphere is washed and an excess of radioactive labeled antibody to ddI is added. The sphere is again washed after an appropriate incubation and the radioactivity bound to the sphere is determined. The amount of radioactivity is inversely proportional to the ddI concentration.

Another preferred heterogeneous immunoassay involves the use of enzyme labels such as horseradish peroxidase, alkaline phosphatase, and $\beta$-galactosidase. The heterogeneous EIA differs from the homogeneous EIA in that determination of the amount of ligand in the sample requires a separation of bound from free tracer not required in the homogeneous EIA. For example, ddI labeled horseradish peroxidase competes with unlabeled ddI for a limited number of antibody combining sites present on antibodies to ddI attached to a solid surface such as a microtiter plate. The ddI antibody may be attached to the microtiter plate directly or attached indirectly by first coating the microtiter plate with multivalent ddI conjugates (coating antigens) prepared for example by conjugating ddI with serum proteins such as rabbit serum albumin (RSA). After separation of the bound labeled ddI from the unbound labeled ddI, the enzyme activity in the bound fraction is determined spectrophotometrically at a fixed period of time after the addition of substrate.

The above examples of preferred heterogeneous immunoassays describe the use of radioactive and enzyme labeled tracers. Alternatively, assays other than EIA that exploit nonisotopic detection systems have been described. These labels include fluorescent materials such as fluorescein, 5-dimethylaminonaphthalene-1-sulfonyl and rhodamine derivatives; phosphorescent materials such as erythrosin and europium chelates; luminescent materials such as luminol and luciferin; and sols such as gold and organic dyes.

Variations to the above described assays designs will be obvious to those skilled in the art.

ddI Compounds

According to this invention, novel derivatives of ddI have been developed for use in the competitive binding assays of this invention as well as for the preparation of such derivatives which can be represented by the general formula:

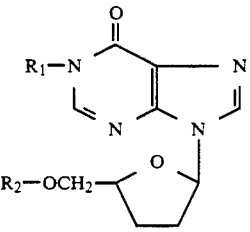

where $R_1$ and $R_2$ are selected from hydrogen and R-A, provided that one of $R_1$ and $R_2$ is hydrogen, R is a linking group, and A is L, X or Y, where L is a leaving group, X is an indicating moiety and Y is a carrier.

ddI Linking Groups

The ddI linking group (spacer) represented by R can be a group of from 0 to 50 atoms other than hydrogen although even larger spacers could be effectively utilized in preparing ddI derivatives by attaching a ddI analog to groups such as oligopeptides, polyamino acids, polymers, carbohydrates and/or cyclic groups as well as by glutaraldehyde copolymerization of aminated ddI analogs with polyamino acids. The atoms comprising R can include from 0 to 30 carbon atoms and from 0-25 hetero atoms selected from oxygen, nitrogen, sulfur and halogen. Generally the atoms of R are present in functional groups as for example alkyl, carbonyl, nonoxocarbonyl, hydroxy, alkoxy, amido, halo, thiocarbonyl, cyano, nitrilo, thio, imino, amino, carbalkoxy, mercuri, phthalimido, formyl, keto, succinimidoxy, thiocarbamyl, azo, hydroxyphenyl, and imidazolyl, as well as other saturated or unsaturated carbocyclic or heterocyclic rings. Preferably R can be from 0 to 30 atoms other than hydrogen including 0 to 20 carbons and 0–10 hetero atoms. More preferably R can be from 1 to 23 atoms other than hydrogen including 1 to 16 carbons and 0–7 hetero atoms. It is even more preferred that R is succindioyl, aminoalkyl or of the structure $-(CH_2)_n-CO-$ or $-(CH_2)_n-NH-$ or $-CO-(CH_2)_n-CO-$, where n is a whole number from 1 to 19, preferably 1 to 8. Even more preferred compositions of R are discussed below with respect to the various groups represented by A. For convenience, the representation of ddI as well as other shorthand designations of various ddI substituents is often used herein in naming various compounds instead of the commonly accepted chemical nomenclature. For example, 2',3'-dideoxyinosine-5'-O-hemisuccinate can be referred to as ddI-5'-hemisuccinate, or simply ddI-5'-HS.

Multivalent ddI conjugates can be used for example in EIAs and NIAs as test, developer or coating antigens, as well as for immunogens and ddI-R-enzyme derivatives. Multivalent ddI conjugates can be made using linking groups R having 1 to 35 atoms comprising 1 to 25 carbon atoms and 0 to 10 hetero atoms. The preferred embodiments for R include up to 7 atoms comprising up to 6 carbon atoms and up to 2 hetero atoms. Illustrative examples of preferred embodiments include:

| (ddI-position)-R:(A) | R (No. of Atoms) | | |
|---|---|---|---|
| | Total (Other than H) | Carbon | Hetero |
| (ddI-1)-(CH$_2$)$_4$—CO: (Bovine Serum Albumin) | 6 | 5 | 1 |
| (ddI-1)-(CH$_2$)$_4$—CO: (Horseradish Peroxidase) | 6 | 5 | 1 |
| (ddI-5')-CO—(CH$_2$)$_2$—CO: (Apoferritin) | 6 | 4 | 2 |

In the case of fluorescent derivatives it should be kept in mind that while, as in the case with other derivatives, there is a theoretical limit to the size of R, when a fluorescent derivative is used in an FPIA that fluorescent derivative should have a molecular weight less than approximately 60,000. Otherwise, free versus bound fluorescent tracer is difficult to distinguish by FPIA. Useful fluorescent derivatives can be prepared where the linking group R is up to 48 atoms comprising up to 24 carbon atoms and up to 24 hetero atoms. Good performance and ease of preparation can be observed for fluorescent derivatives having R groups of up to 14 atoms comprising up to 8 carbon atoms and up to 6 hetero atoms. The preferred embodiments of fluorescent derivatives have up to 8 atoms comprising up to 5 carbon atoms and up to 3 hetero atoms. Examples of such preferred fluorescent derivatives include:

| (ddI-position)-R:(A) | R (No. of Atoms) | | |
|---|---|---|---|
| | Total (Other than H) | Carbon | Hetero |
| (ddI-1)-(CH$_2$)$_3$—CO—NH: (Fluorescein) | 6 | 4 | 2 |
| (ddI-1)-(CH$_2$)$_3$—NH—CS—NH: (Fluorescein) | 7 | 4 | 3 |

The tracer also can be radioactive. In that case, the preferred linking group R can be up to 40 atoms, of which there could be up to 30 carbon and up to 15 hetero atoms. With radioactive ddI tracers it should be noted that when using $^3$H as the indicating group, $^3$H can be substituted directly into ddI or any ddI analog as well as being attached to another compound that is subsequently attached to ddI.

Attachment of R to the hapten (ddI) can occur at any one of several available sites in the ddI molecule. Generally, the most satisfactory tracers are obtained when R is attached at the same position of the hapten molecule to which the linking group was attached when preparing the immunogen. Furthermore, the linking group R can be the same for the tracer and the immunogen (homologous linking groups). For example, tracers for RIAs are frequently prepared from the same haptenic analog used for preparing the immunogen. Hence, R will be the same in both cases. There are instances, however, in which a different linking group will be needed in the tracer than was used in the immunogen (heterologous linking groups) in order to provide an acceptable assay. One reason for using heterologous linking goups is that when the linking group is identical in both the tracer and immunogen (homologous linking groups) the resulting antibodies tend to show a significantly greater affinity for the tracer than for the native or underivatized hapten (i.e., the analyte), thus reducing the ability of the analyte to compete effectively with the tracer in an assay, resulting in loss of assay sensitivity. The need for heterologous linking groups is especially pronounced for tracers intended for FPIAs since small variations in R have a great effect on the tracer-antibody binding properties in an FPIA.

The selection of a heterologous linking group is a complex problem involving many considerations including:

1. The functional group in the hapten (ddI) or in the leaving group (L) or indicator moiety (X) or carrier (Y), to be modified;

2. Composition of the linking group in the immunogen;

3. Method of attaching the linking group (R) to ddI and either L or X or Y which may necessitate modifying ddI and/or L or X or Y prior to linkage so that R of the final product may be comprised in whole or in part of these modifications;

4. Composition of the linking group being considered including length, nature (aliphatic, carbocyclic, aromatic, heterocyclic), hetero atoms and other functional groups present;

5. Availability of starting materials;

6. Means for isolating, purifying and characterizing the haptenic analog or derivative;

7. Assay protocol; and

8. Quantity and binding properties of the antibody available.

Therefore, it is often advantageous to prepare a number of possible tracers having linking groups of varying composition (see item 4 above) and select the one providing the most desirable standard curve for a given method and antibody.

Leaving Group

A leaving group is one or more atoms that is given up by a compound during the reaction of that compound with another chemical. In the case of the present invention, a leaving group is given up in the synthesis of analogs (from other analogs or ddI) and derivatives, such as immunogens and tracers.

The leaving group, L, can be hydrogen, hydroxy, halo, sulfonyloxy, or a group containing 1-8 carbons selected from, but not limited to, alkyl, alkoxy, acyl, or succinimidoxy moieties. The leaving groups can also, for example, include phthalimido [Reaction (1) below] or carbobenzoxy [Reaction (2) below] groups which decompose on removal, as shown in the following reaction schemes:

Reaction 1

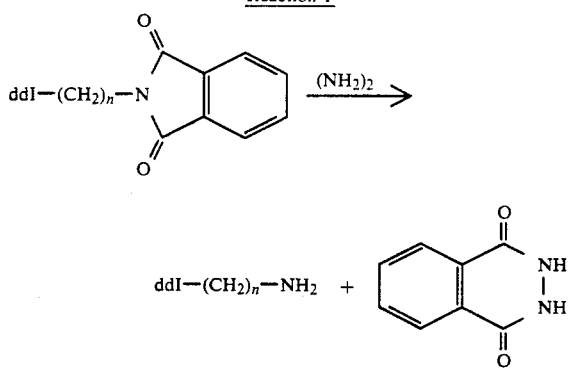

Reaction 2

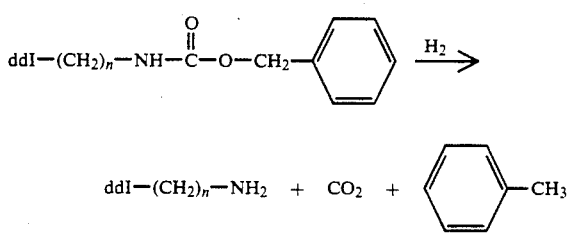

ddI Immunogens

A basic requirement common to all immunoassay methods is an antibody raised to the ligand or a closely related ligand analog. Since ddI (hapten) is a ligand that is unlikely to be immunogenic per se, it is converted to an analog, as described above, and subsequently conjugated to a carrier which is immunogenic in animals. Preferably, the carrier will be a protein type including albumins, serum proteins, e.g., globulins and lipoproteins. Illustrative proteins include bovine serum albumin, keyhole limpet hemocyanin, egg ovalbumin and bovine gamma-globulins. Synthetic polyamino acids also can be used provided they have a sufficient number of suitable groups. These conjugates can be prepared by carbodiimide mediated dehydrations as well as by many other conjugation methods. However, it is preferable when possible to prepare these conjugates by acylation of amines with active esters since a higher incorporation rate of ddI analog to carrier is likely, resulting in a better immunological response to the immunogen.

Analogs or derivatives of ddI can be prepared through any one of several different positions of ddI including the 1, 5', 8, 2', 3', 2, 3, 7, or 6 positions (listed in order of preference). While substitution of ddI is more easily accomplished through the 5' position, analogs or derivatives prepared through the 1 position of ddI are preferred because immunogens made from 1 position ddI analogs are more likely than immunogens made from 5' position ddI analogs to produce antibodies less cross-reactive to the major metabolites of ddI.

Analogs containing a carboxyl function (sometimes hereinafter referred to as carboxylic acid analogs) are preferred to analogs containing an amino function (sometimes hereinafter referred to as amino analogs) in the preparation of immunogens because the carboxylated analogs can be converted to active esters which can react with the free amino groups present in protein, assuming protein is used as the carrier. Alternatively, carboxylated ddI haptens can be coupled to proteins directly using carbodiimide (CDI) methods. In the case of carboxylic acid ddI analogs, CDI will activate the carboxyl groups on both the hapten analog and the protein which will compete for binding to the free amino groups of the protein. Similarly, in the case of amino ddI analogs, CDI will activate the carboxyl groups of the protein resulting in competition between the free amino group of the hapten and the free amino groups of the protein for binding to the activated carboxyl groups of the protein. In both cases, the use of CDI typically results in a lower incorporation rate of hapten to carrier than when a carboxylic acid active ester analog is used and activation of carboxyl groups on the protein by CDI leads to increased cross-linkage between proteins and accompanying masking of attached haptens within the cross-linked conjugates. Preferred immunogens are prepared by reacting carrier proteins to active esters of ddI formed via carboxyl bearing substituents at the 1 position of ddI.

In preparing an immunogen, the size of the hapten involved in part affects the desired length of the spacer R connecting the hapten and the carrier. For a relatively large hapten, such as digoxin, the length of the spacer is not very important since the binding sites of the antibodies produced are only able to bind a portion of the hapten. However, in the case of a relatively small hapten such as ddI, antibody binding sites would be able to bind to most of the hapten. Consequently, it is desirable to have the antibody producing cells (lymphocytes) better able to "recognize" the hapten without steric interference from the carrier. Better recognition generally results in the production of antibodies having lower cross-reactivities to compounds other than the hapten as well as having higher affinities for the hapten and thus greater assay sensitivity to the hapten.

Preferably immunogens can have a spacer of up to 7 atoms other than hydrogen to produce antibodies to ddI. More preferably the spacer for immunogens can have a chain length of from four to five atoms, e.g. (ddI-1-valeryl:BSA (ddI-1-V:BSA) and ddI-5'-succinyl:BSA (ddI-5'-S:BSA). With a greater though still reasonable amount of optimization, operable antibodies could be produced from immunogens having a spacer having from 1 to 23 atoms other than hydrogen. It should be kept in mind that even longer spacer chain lengths could be effectively utilized in preparing immunogens by attaching ddI or a ddI analog to long chain groups such as oligopeptides or to heterocyclics.

Generally, the carrier utilized in forming the immunogen is a polyamino acid which can be naturally occurring or synthetic and is usually an immunogenic polypeptide or protein. The polyamino acid can comprise constituents in addition to amino acids and will usually be of a molecular weight between about 5,000 and 5,000,000, preferably between about 15,000 and 4,000,000, and more preferably between about 30,000 and about 3,000,000. Carbohydrates, e.g., polysaccharides, liposomes and the like also can be used. Particularly useful proteins are albumins, globulins, enzymes, hemocyanins, proteins having significant non-proteinaceous constituents, e.g., glycoproteins, and the like. Preferred examples of carrier proteins which can be used to prepare the conjugate (immunogen) are bovine serum albumin (BSA), keyhole limpet hemocyanin (KLH), and *Limulus polyphemus* hemocyanin (LPH). Albumins and globulins having a molecular weight between about 30,000 and about 200,000 are particularly preferred.

The preparation of the immunogens or conjugates can be accomplished by means known to the art. See for example, *Principles of Competitive Protein-Binding Assays, Second Edition,* Odell et al, editors, John Wiley and Sons, New York, 1983, Chapter 4, Conjugation Techniques-Chemistry, and the references discussed therein.

ddI Antibodies

The preparation of specific antibodies using the present immunogens can be accomplished by techniques known to those skilled in the art. In the usual case, a host animal such as rabbit, goat or mouse is injected at one or more sites with an immunogen, normally emulsified with an adjuvant. Further injections are made at the same or different site or sites at regular or irregular intervals.

As is known, an animal's immune system will respond to immunization by producing antibodies that will react with one or more epitopes of the conjugate. Each plasma cell clone secretes a unique antibody (idiotype).

Monoclonal antibodies can be produced in vitro by physically separating the individual plasma cell clones which have been hybridized with a tumor cell line, thus enabling one to produce antibodies of a selected idiotype for an extended period of time.

In the animal, generally multiple plasma cell clones are produced, resulting in a heterogeneous mixture of antibodies (i.e., polyclonal antibodies) in the blood.

After the blood has been collected, it will clot and the clot may be removed. The remaining liquid or serum, which contains the polyclonal antibodies may then be referred to as antiserum.

Although generally not required, purification of the antiserum may be instituted where it is found desirable to remove undesired material such as non-specific antibodies before the antiserum is considered suitable for use in performing assays.

It is to be noted that while monoclonal antibodies from a particular monoclonal line developed are identical and the polyclonal antibodies obtained from a particular animal injected are similar, variance in antibody binding properties does exist between antibodies from different monoclonal lines and/or different animals injected. Identical construction of the ddI analog portion of the tracer and of the immunogen can result in antibody binding to the tracer so great that ddI can not effectively compete with the tracer for binding to the antibody. Accordingly, when an antibody population is evaluated using other than $^3H$ tracers, a number of tracers are made in which the length and/or composition of the spacer linking the indicator moiety to ddI is varied in order to optimize the binding properties of the antibodies versus the tracer and ddI.

ddI Tracers

The preparation of the tracers of this invention from ddI analogs involves the coupling of the analog with a suitable indicator or indicator derivative. Coupling can be accomplished by means known to the art. Furthermore, from the above description of the assay of this invention it is evident that the indicator moiety is not critical to the invention and can be selected by those skilled in the art based upon the various criteria previously discussed. Tracers contemplated include those obtained by coupling a ddI analog to a fluorescent, radioactive, phosphorescent, chemiluminescent, bioluminescent, free radical or similar moiety as well as to polypeptides such as enzymes or proteins, polymers such as latex, polysaccharides such as polydextran, receptors, cofactors and enzyme inhibitors.

To prepare the tracers of this invention an analog of ddI is first prepared in such a fashion that the analog has one or more antigenic determinant sites capable of binding a receptor (ddI antibody) during the course of the immunoassay. A characteristic of such ddI analog is, therefore, that it possesses sufficient structural similarity to ddI so as to be recognized by the antibody to ddI. The ddI analog can then be used to prepare the tracers of this invention as well as to prepare the immunogens used for generation of the antibodies of this invention.

Assuming a carboxylated analog of ddI is used to prepare the immunogen, then an amino analog would be one preferred for use in preparing a tracer if such analog can be prepared in a reasonable yield. In general, amino analogs are more difficult to prepare than carboxylated analogs. For example, in the case where ddI-1-V:BSA (Example 3) is the immunogen then a 1 position amino analog of ddI would be one preferred analog for use in preparing tracers. The difference in appearance between the tracer and the immunogen serves to minimize binding of antibodies based on spacer similarity and so results in better assay sensitivity since the antibodies will be selected based on their affinity to ddI and not the spacer. In addition, this necessary selection of antibodies specific to ddI can result in the affinity of the antibodies to ddI versus the tracer being more nearly equal which is generally desirable in a competitive binding immunoassay.

Isothiocyanates, acid chlorides and active esters generally react spontaneously with amines. Furthermore, isothiocyanates of many fluorochromes are readily available. Because fluorescein isothiocyanate (FITC) derivatives are widely used in fluorescence immunoassay techniques, including FPIAs, a 1 position amino analog of ddI reacted with FITC is one of the preferred means of preparing such tracers as well as providing a preferred tracer. Whether FITC Isomer I, or Isomer II, or a mixture thereof, is chosen is dependent upon the particular antibodies produced and the empirical data developed with such antibodies. FITC Isomer I and Isomer II are distinguished by the fact that the isothiocyanate group is attached to the fluorescein in the 5 or 6 position, respectively. This discussion also applies to Isomer I and II of fluoresceinamine, fluoresceinamine derivatives and erythrosin. The following structure:

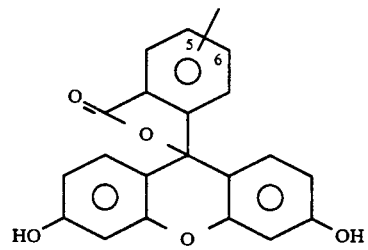

depicts attachment of fluorescein at the 5 or 6 position.

While FITC is a derivative of fluorescein, other derivatives of fluorescein as well as other fluorochromes including derivatives of rhodamine and derivatives of 5-dimethylaminonaphthalene-1-sulfonic acid can also be used. Those fluorochromes may be homogenous compounds or isomeric mixtures. Also, they may be used in any lactone form or as any biologically acceptable salts.

As used herein, the term "biologically acceptable salts" refers to salts such as the sodium, potassium, ammonium, phosphate and chloride salts, and the like, which will enable the tracers of the invention to exist in their ionized state when employed in the method of the present invention. Generally, the tracers will exist in solution as salts as a result of the buffer employed, e.g., in the presence of a sodium phosphate buffer the tracers will generally exist in their ionized state as a sodium salt.

Examples of derivatives of fluorescein other than FITC which are preferred include fluoresceinthiocarbamylethylenediamine (FTED) or fluoresceinamine (FAM) or dichlorotriazinylaminofluorescein (DTAF) or methoxychlorotriazinylaminofluorescein (MTAF) or aminomethylfluorescein (AMF), fluoresceinthiosemicarbazide or carboxyfluorescein for use in FIA or FPIA. Also, there are immunoassay techniques requiring indicator groups which can be more easily prepared by reactions other than via amino derivatives of ddI with isothiocyanates, acid chlorides or active esters. Such indicator groups include apoferritin or rabbit serum albumin (RSA) for use in an EIA or NIA. In order to prepare tracers with such other labeling groups it is preferable to use 1 position carboxylated analogs of ddI. It is further preferred that an active ester be prepared from a carboxylated analog of ddI for subsequent reaction with the labeling group rather than activating the carboxyl group of the ddI analog with CDI for direct reaction with the labeling group. This is because in the case of labeling groups other than proteins, tracers obtained from CDI mediated reactions between the ddI analog and the labeling group will require more purification and accompanying loss of yield. In the case of proteins such as apoferritin and RSA, use of CDI will result in more cross-linkage between proteins and corresponding masking of the attached hapten (ddI) within the cross-linked conjugate so that less of the hapten is available for use in the immunoassay.

Specifically, in terms of FTED derivatives, an active ester can be used to prepare, for example, ddI-1-valeryl:FTED and ddI-1-butyryl:FTED. On the other hand, the amino group of FAM is not sufficiently nucleophilic to allow satisfactory reaction with an active ester of a carboxylated ddI analog. As a result, CDI can be used to directly mediate the reaction of FAM with a carboxylated ddI analog.

It should be noted that fluorescein derivatives can be radioactively labeled in order to provide tracers for RIAs.

As was previously discussed regarding immunogens, the preparation of a test or coating antigen, for example, for an NIA or EIA, can be accomplished by reacting the active ester of a carboxyl analog of ddI with a protein such as apoferritin or RSA.

For example, ddI-1-MV (Example 1) is first prepared, which is then subjected to base catalyzed hydrolysis to produce ddI-1-VA (Example 2), followed by reaction of ddI-1-VA with N-hydroxysuccinimide (NOS) to provide ddI-1-V:NOS (See Example 4). ddI-1-V:NOS can then be converted to its rabbit serum albumin derivative, ddI-1-V:RSA, which can then be used as the test or coating antigen in the assay. This rabbit serum albumin derivative also can be used as the developer antigen in nephelometric inhibition immunoassays.

Test Kits

In addition to the foregoing, the present invention includes the provision of diagnostic test kits suitable for being utilized with minimal user preparation in connection with the various assays described above. Such kits can be used for the determination of the presence or absence of ddI in a sample of biological fluid as well as determining the level of ddI in a sample containing ddI. These kits will generally be a set of optimized reagents comprising the combination of antibodies specific to ddI and tracer capable of reacting with the antibodies to produce a detectable antibody-tracer reaction, whereby the antibodies can be intermixed with a sample of biological fluid to be tested and the tracer, and then subjected to the appropriate technique for indicating the presence of ddI and/or the level of ddI in the sample.

In addition, the diagnostic test kits of this invention can optionally contain a precipitating agent, as described herein, suitable for reducing nonspecific background interference, for example fluorescence, due to the presence of various materials in the sample to be analyzed. The test kit can also be supplied with a buffer, as appropriate for the particular assay to which the kit is directed. The test kit can further be supplied with means for separating the antibody-tracer complex from unbound or free tracer in the case where the kit's assay method is heterogeneous as described herein.

Synthesis of ddI Compounds

To further illustrate the foregoing discussion, representative reactions which can be used in various reaction schemes include the following:

A. Acylation of alcohols with cyclic dicarboxylic anhydrides. For example, succinic anhydride reacts with an alcohol to give the corresponding hemisuccinate. Glutaric anhydride can be used in place of succinic anhydride to obtain the glutardioyl analog. The reaction is preferably conducted in an aprotic organic solvent. Pyridine and/or dimethylaminopyridine are commonly used as catalysts.

B. Alkylation of nucleophiles. Alkylation of nucleophiles can be performed using a halogenated reactant, Hal—$CH_2$—R, usually where Hal is bromine, or using a sulfonate.

C. Carbodiimide-mediated dehydrations. Carbodiimides (CDIs) mediate reactions between carboxylic acids and amines resulting in the formation of amides, including peptides. For example, carboxylated analogs of ddI can be condensed with the amino group of various isomers of fluoresceinamine in the presence of 1,3-dicyclohexylcarbodiimide (DCC) or 1,3-diisopropylcarbodiimide, or such ddI analogs can be reacted with the free amino groups of proteins in an aqueous environment if a water soluble reagent, such as 1-ethyl-3-(3-dimethylaminopropyl)-carbodiimide hydrochloride, (ECDI) is employed. DCC can also be used to condense carboxylated ddI analogs with reagents, including N-hydroxysuccinimide (NOS), N-hydroxysulfosuccinimide or salts of N-hydroxysulfosuccinimide for the purpose of preparing active esters useful in the acylation of amines.

D. Acylation of amines by active esters. Active esters derived from carboxylated analogs of ddI and leaving groups such as N-hydroxysuccinimide, react with aliphatic amines, such as a carrier protein, resulting in the elimination of the leaving group and simultaneous formation of an amide (peptide) bond.

E. Base catalyzed hydrolysis of alkyl esters to provide a carboxylic acid upon acidification.

F. Hydrazinolysis of phthalimides to provide aminoalkyl analogs of ddI. By reacting phthalimidoalkyl substituted ddI (prepared for example, by the reaction of ddI and a bromoalkyl phthalimide) with hydrazine hydrate, amino terminal haptens are provided. These analogs are quite useful for preparing a variety of other ddI derivatives, as will be appreciated by those skilled in the art, due to the reactivity of the $NH_2$ group. For example, such analogs will react with isothiocyanates, active esters, acid halides, or other electrophilic reagents. They also can be reacted with proteins in the presence of carbodiimide and a variety of other reagents.

G. Addition of amines to isothiocyanates. This general reaction is useful for preparing fluorescein, rhodamine and similar conjugates, since the isothiocyanates of those fluorochromes are commercially available. Such labeling reagents may be homogenous compounds or isomeric mixtures.

H. Iodination of phenols. Electrophilic iodine ($I_2$) attaches itself to phenols in the 2, 4, or 6 position (relative to the phenolic hydroxyl group) unless these positions are blocked by other substituents. This reaction is useful for radioiodinating some hapten analogs to produce radioactive derivatives for use in radioimmunoassays. The iodine can be purchased from commercial sources as non-volatile Na-($^{125}$I) or Na-($^{131}$I) which is mixed with the phenol to be radioiodinated. An oxidizing agent, e.g. chloramine-T, is then used to convert the iodide to $^{125}I_2$ or $^{131}I_2$ which then attaches to the aromatic ring. Traditionally, tyrosine methyl ester (TME) analogs are used for iodination.

I. Nucleophilic aromatic substitution. Amines displace halides from suitably activated, halogenated aromatic or heterocyclic systems.

J. Halogenation of purines. Purine nucleosides can be halogenated in position 8. The reaction is usually carried out with bromine in acetate buffers below pH 7. The reaction is of value because in a subsequent reaction the halogen can be replaced by nucleophiles such as ethylenediamine to produce amino-terminal analogs. Amino-terminal analogs are useful intermediates since such analogs can react with electrophilic molecules such as isothiocyanates, carboxylic acids and acid chlorides.

Representative reaction schemes for the preparation of analogs, immunogens and tracers of this invention are outlined below. For convenience, the representation ddI is used instead of commonly used chemical nomenclature.

A representative reaction scheme for introducing carboxy terminal substituents into the 1 position of ddI is as follows:

1. ddI is reacted with methyl-5-bromovalerate (Reaction B) to provide 5-(2',3'-dideoxyinosin-1-yl)-valeric acid methyl ester (ddI-1-MV) (Example 1).

2. The product from step 1 is hydrolyzed (Reaction E) to provide 5-(2',3'-dideoxyinosin-1-yl)-valeric acid (ddI-1-VA) (Example 2).

3. The product of step 2 is reacted with NOS (Reaction C) to provide N-[5-(2',3'-dideoxyinosin-1-yl)-valeroxy]-succinimide (ddI-1-V:NOS) (See Example 4).

4. The product of step 3 can be reacted with FTED (Reaction D) to provide the labeled reagent 5-[2-[5-(2',3'-dideoxyinosin-1-yl)-valeramido]-ethylthiocarbamyl]-fluorescein (ddI-1-V:FTED).

As an alternative, the product of step 2 can be reacted with fluoresceinamine (FAM) (Reaction C) to provide the reagent 5-[5-(2',3'-dideoxyinosin-1-yl)-valeramido]-fluorescein (ddI-1-V-FAM). Also, the product of step 3 can be reacted with TME (Reaction D) to provide 2-[5-(2',3'-dideoxyinosin-1-yl)-valeramido]-3-(4-hydroxyphenyl)-propionic acid methyl ester (ddI-1-V:TME) which in turn can be reacted with $^{125}$I (Reaction H) to provide the tracer 2-[5-(2',3'-dideoxyinosin-1-yl)-valeramido]-3-(4-hydroxy-3-[$^{125}$I]-iodoph enyl)- propionic acid methyl ester or 2-[5-(2',3'-dideoxyinosin-1-yl)-valeramido]-3-(4-hydroxy-3,5-[$^{125}$I]-diiodophenyl)-propionic acid methy l ester or mixture of the two (ddI-1-V:TME-[$^{125}$I]$_n$), where n is 1 or 2.

Furthermore, the product of step 3 can be used to prepare any number of immunogens using Reaction D as, for example, by reaction with keyhole limpet hemocyanin (KLH) or bovine serum albumin (BSA). In addition, the product of step 3 can be reacted with the enzyme, horseradish peroxidase (HRP), using Reaction D, to prepare an enzyme labeled derivative of ddI that can be used as a tracer in an enzyme immunoassay. Also, the product of step 3 can be reacted with rabbit serum albumin (RSA) using Reaction D, to provide a test antigen for detecting ddI antibodies, as a coating antigen, or as a developer antigen for an NIA.

Similarly, other 1 position analogs, e.g., butyryl, propionyl or acetyl analogs, immunogens and derivatives of ddI can be prepared by similar reaction schemes to that described above for ddI-1-valeryl compounds. For example, ethyl-4-bromobutyrate or bromoacetic acid can be used instead of methyl-5-bromovalerate. Fluorescent tracers that can be made in this manner include 5-[2-[4-(2',3'-dideoxyinosin-1-yl)-butyramido]-ethylthiocarb amyl]-fluorescein (ddI-1-B:FTED) and 5-[4-(2',3'-dideoxyinosin-1-yl)-butyramido]-fluorescein (ddI-1-B-FAM).

If aminoalkyl analogs and derivatives are desired, a suitable reaction scheme can be as follows:

1. ddI can be reacted with N-(2-bromoethyl)-phthalimide (Reaction B) to provide 1-(2-phthalimidoethyl)-2',3'-dideoxyinosine (1-PHT-E-ddI).

2. The product from step 1 can then be subjected to hydrazinolysis (Reaction F) to provide 1-(2-aminoethyl)-2',3'-dideoxyinosine (1-AE-ddI).

3. The product of step 2 can be reacted with 5-[(4,6-dichloro-s-triazin-2-yl)-amino]-fluorescein (DTAF) to provide 1-[2-[4-[(fluorescein-5-yl)-amino]-6-chloro-s-triazin-2-yl]-am inoethyl]-2',3'-dideoxyinosine (1-AE-ddI:DTAF) (Reaction I).

4. The product of step 2 also can be reacted with 5-[4-chloro-6-methoxy-s-triazin-2-yl)-amino]-fluorescein (MTAF) to provide 1-[2-[4-[(fluorescein-5-yl)-amino]-6-methoxy-s-triazin-2-yl]-aminoethyl]-2',3'-dideoyxyinosine (1-AE-ddI:MTAF) (Reaction I).

5. Alternatively, the product of step 2 can be reacted with fluorescein isothiocyanate (FITC) (Reaction G) to provide 5-[2-(2',3'-dideoxyinosin-1-yl)-ethylthiocarbamyl]-fluorescein (1-AE-ddI:FITC). Similarly, the product of step 2 can be reacted with erythrosin isothiocyanate (EITC).

The product of step 2 also can be reacted with 3-(p-hydroxyphenyl)-propionic acid N-hydroxysuccinimide ester (Reaction D) to prepare 1-[2-[3-(4-hydroxyphenyl)-propionamido]-ethyl]-2',3'-dideoxyinosine (1-AE-ddI:HPPA), which can in turn be converted to the radioactive tracer 1-[2-[3-(4-hydroxy-3-[$^{125}$I]-iodophenyl)-propionamido]-ethyl]-2',3'-dideoxyinosine or 1-[2-[3-(4-hydroxy-3,5-[$^{125}$I]-diiodophenyl)-propionamido]-ethyl]-2',3'-dideoxyinosine or a mixture of the two (1-AE-ddI:HPP-[$^{125}$I]$_n$, wherein n is 1 or 2, by reaction with $^{125}$I (Reaction H). Alternatively, the product of step 2 can be directly iodinated by reaction with the iodinated active ester (N-succinimidyl-3-(4-hydroxy-3-[$^{125}$I]-iodophenyl)-propionate, or N-succinimidyl-3-(4-hydroxy-3,5-[$^{125}$I]-diiodophenyl)-propionate or a mixture thereof using Reaction D to provide the same compounds mentioned above. Besides preparing iodinated tracers from ddI analogs having a phenolic group, other compounds capable of being iodinated can also be prepared from the product of step 2 as, for example, by reaction with carboxylated imidazoles using Reaction C.

Some fluoroescent 1 position ddI derivatives that can be prepared using the various reaction schemes described above can be summarized as follows:

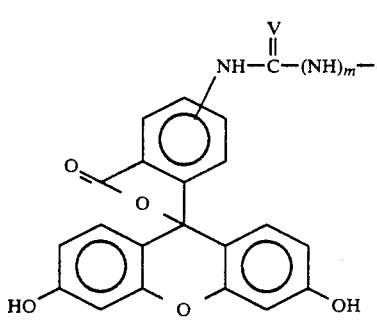
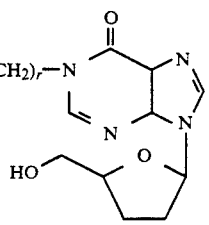

where V is oxygen or sulfur; m is 0 or 1; n is 0 through 8; p is 0 or 1; q is 0 or 1; and r is 1 through 8; except that if m and p are both 1 then n cannot be 1.

For preparing 5' position analogs and derivatives the following reaction schemes can be used.

1. ddI is acylated with succinic anhydride to provide ddI-5'-hemisuccinate (ddI-5'-HS) (Reaction A)

2. The product from step 1 can be reacted with N-hydroxysuccinimide (NOS) to provide N-[(2',3'-dideoxyinosin-5'-yl)-succinyloxy]-succinimide (ddI-5'-S:NOS) (Reaction C).

3. The product from step 2 can be reacted with tyrosine methyl ester (TME) to provide 2-[(2',3'-dideoxyinosin-5'-yl)-succinamido]-3-(4-hydroxyphenyl)-propionic acid methyl ester (ddI-5'-S:TME) (Reaction D).

4. Also, the product from step 3 can be reacted with $^{125}$I to provide the reagent, 2-[(2',3 -dideoxyinosin-5'-yl)-succinamido]-3-(4-hydroxy-3-[$^{125}$I]-iodophenyl)-propionic acid methyl ester or 2-[(2',3'-dideoxyinosin-5'-yl)-succinamido]-3-(4-hydroxy-3,5-[$^{125}$I]-diiodophenyl)propionic acid methyl ester or a mixture of the two (ddI-5'-S:TME-[$^{125}$I]$_n$), where n is 1 or 2 (Reaction H).

Alternatively, the product from step 1 can be reacted in the presence of carbodiimide with fluoresceinamine (FAM) (Reaction C) to provide 5-[2',3'-dideoxyinosin-5'-yl)-succinamido]-fluorescein (ddI-5'-S:FAM). An additional alternative is to react the product from step 2 with 5-[N'-(2-aminoethyl)-thioureido]fluorescein (fluoresceinthiocarbamylethylenediamine) (FTED) (Reaction D) to provide the tracer 5-[2-(2',3'-dideoxyinosin-5'-yl-succinamido)-ethylthiocarbamyl -fluorescein (ddI-5.-S:FTED).

Furthermore, the product of step 2 can be reacted with bovine serum albumin (Reaction D) to provide an immunogen or reacted with a carrier other than bovine serum albumin, such as rabbit serum albumin or horse spleen apoferritin (Reaction D), to provide a test antigen, which in turn can be used to detect ddI or ddI specific antibodies. For example, the test antigen can be used as a coating antigen for enzyme linked immunosorbent assays (ELISA), or as a developer antigen for nephelometric inhibition immunoassays (NIA).

For preparing 8 position analogs and derivatives, the following reaction schemes can be used.

1. ddI is reacted with bromine in acetate buffer to give 8-bromo-2',3'-dideoxyinosine (8-Br-ddI) (Reaction J).

2. The product from step 1 can then be reacted with ethylenediamine to give 8-(2-aminoethyl -2',3'-dideoxyinosine (8-AE-ddI) (Reaction B).

3. Alternatively, the product from step 1 also can be reacted with mercaptoacetic acid to give 2',3'-dideoxyinosine-8-(carboxymethyl)-thioether (8-CMT-ddI) (Reaction B).

The product from step 2 can be used as starting material for preparing the same kinds of compounds obtained from 1-AE-ddI. The product from step 3 can be condensed with FAM (Reaction C) or with NOS and FTED (Reaction D).

The following nonlimiting examples are provided to further demonstrate to those skilled in the art the preparation of specific ddI analogs, immunogens, antibodies and labeled analogs as well as methods for determining concentration of ddI within the scope of this invention. The quantities indicated for the solvent systems employed in the chromatographic analyses are volume ratios. Thin layer chromatography (TLC) plates used included Silica Gel F (SGF) and Reversed Phase F (RPF) having thicknesses including 250 μm, 1,000 μm or 2,000 μm. TLC plates were visualized after development using short wave UV (254nm), long wave UV (366nm), or visible light as appropriate, unless otherwise specified.

EXAMPLE 1

5-(2',3'-dideoxyinosin-1-yl)-valeric acid methyl ester (ddI-1-MV)

To 533 mg ddI in 1 ml of sieve-dried N,N-dimethylacetamide (DMA) was added 400 μl of methyl-5-bromovalerate (MBV) and 1 ml of a 4.4M methanolic solution of sodium methoxide (this methanolic solution will be referred to as NaOMe). The resulting clear solution was heated at 75° for 30 minutes, when 200 μl each of MBV and NaOMe were added, followed by heating 40 minutes at 75°. Then 200 μl each MBV and NaOMe were added each hour for 3 hours, keeping the reaction temperature at 75°. Finally, 100 μl each of MBV and NaOMe were added, followed by heating 1 hour at 75°. A total of 1.3 ml MBV and 1.9 ml NaOMe were used and total heating time (at 75°) was 310 minutes.

The reaction mixture was diluted with 40 ml water, the pH adjusted to 7.2 with 1N HCl and the crude product was extracted into 10×40 ml EtOAc. The organic phase was concentrated and purified by preparative TLC on silica gel-F, 2000 μm (SGF-2000). The developing solvent was MeOH/CHCl$_3$ (10+90) and R$_f$ of the product was about 0.4. The purified product was eluted with MeOH. Alkylation at position 1 was confirmed by kinetic and spectroscopic methods.

EXAMPLE 2

5-(2′,3′-dideoxyinosin-1-yl)-valeric acid (ddI-1-VA)

Approximately 240 mg of TLC-purified ddI-1-MV (Example 1) in 20 ml MeOH was treated with 100 μl of 19M NaOH and heated at 65° C. for 1.5 hours, then concentrated to about 2 ml under reduced pressure, keeping the temperature below 55°. The concentrate was chromatographed on two SGF-2000 TLC plates with MeOH/Et$_3$N (100+0.2). The major band (R$_f$=0.5) was eluted with MeOH, concentrated to 3 ml under reduced pressure and a trace of Et$_3$N was added to bring the pH above 7. The product was homogeneous in three analytical TLC systems:

a) SGF-250 CHCl$_3$/MeOH/HOAc (87.5+12.5+0.33); R$_f$=0.24
b) SGF-250 MeOH/Et$_3$N (100+0.2); R$_f$=0.44
c) RPF-250 MeOH/H$_2$O (10+90); R$_f$=0.46

The UV spectrum of the product in PBS (0.1M NaPO$_4$/0.15M NaCl/pH 7.4) showed an absorbance maximum at 251 nm and the shoulder at about 275 nm, characteristic of 1-substituted inosines, was clearly evident.

EXAMPLE 3 ddI-1-V:BSA Immunogen

Fifty-six milligrams of N-hydroxysulfosuccinimide sodium salt was suspended in 1 ml of DMA containing approximately 150 μmoles of ddI-1-VA (Example 2). The suspension was chilled on an ice-MeOH bath; 500 μl of 1M 1,3-dicylohexylcarbodiimide (DCC) in THF was added and stirring was continued for 10 minutes on the bath, then overnight at room temperature. The resulting suspension was added in 50 μl aliquots with vigorous stirring to a solution of 60 mg bovine serum albumin (BSA) in 7 ml of water to which 3 ml of 0.15M borax-HCl pH 8.5 was added. The suspension was incubated at 4° for 48 hours with occasional stirring and clarified by centrifugation, then filtering the supernatant through a 0.8/m membrane. The resulting solution was then chromatographed over Sephadex G-25 ®, eluting with PBS. The yield was 86% (biuret) and an average of 21 moles of hapten were coupled per 66,000 g of protein, assuming a molar extinction coefficient of 10,400 at 251 nm for the hapten.

EXAMPLE 4

5-(2′,3′-dideoxyinosin-1-yl)-valeryl:peroxidase enzyme label (ddI-1-V:HRP)

To a solution of 45 mg (140 μmoles) ddI-1-VA (Example 2) in 1 ml DMA was added 56 mg (466 μmoles) N-hydroxysuccinimide. The solution was chilled on an ice-isopropanol bath, 500 μl of 1M DCC in THF was added, and after 10 minutes the bath was removed and the reaction mixture was stirred overnight at room temperature when TLC indicated about 60% esterification.

A solution of 10 mg horseradish peroxidase (HRP) in 1 ml of 0.15M borax-HCl pH 8.5 was cooled on an ice-water bath and treated with 100 μl of the reaction mixture described in the above paragraph. After stirring 60 minutes on the ice bath the mixture was filtered through a 0.45 μm membrane and chromatographed over Sephadex G-25 ®.

EXAMPLE 5

4-(2′,3′-dideoxyinosin-1-yl)-butyric acid ethyl ester (ddI-1-EB)

A suspension of 550 mg (233 μmoles) of ddI in 4 ml of dry DMA was treated with 100 μl of ethyl-4-bromobutyrate (EBB) and 100 μl of 4.4M sodium methoxide in MeOH (NaOMe) and heated at 75° for 15 minutes. Another 100 μl each EBB and NaOMe were added followed by heating 30 minutes at 75°. The latter was repeated five times so that a total of 600 μl EBB and 600 μl NaOMe was added. The solution experienced a total heating time of about three hours during this addition. The reaction was followed by TLC using SGF-250 CHCl$_3$/MeOH (90+10). The Rf of the product was 0.4 and ddI (R$_f$=0.16) was no longer present after heating three hours. The reaction mixture was diluted with 40 ml of water and the pH adjusted to 7.2 with 1N HCl, then extracted with 10×40 ml EtOAc. After drying the organic phase with Na$_2$SO$_4$, the EtOAc extract was concentrated to about 4 ml and chromatographed over four SGF-1000 TLC plates using the solvent CHCl$_3$/MeOH (90+10) and the product (main band, R$_f$=0.4) was eluted with MeOH containing sufficient Et$_3$N to keep the pH between 7 and 8. The solvent was then evaporated to dryness under reduced pressure and excess Et$_3$N coevaporated with fresh MeOH. The compound, dissolved in PBS, showed an absorbance maximum of 251 nm with a shoulder at about 275 nm. It was also shown to have immunologic activity versus rabbit antiserum (Example 9) to ddI-1-V:BSA (Example 3) by RIA using $^3$H-ddI.

EXAMPLE 6

4-(2′,3′-dideoxyinosin-1-yl)-butyric acid (ddI-1-BA)

Approximately 1.5 mmoles of TLC-purified ddI-1-EB (Example 5) in 15-20 ml of MeOH was treated with 100 μl of 19N NaOH and heated at 65° for 1.5 hours. The mixture was concentrated to about 2 ml under reduced pressure, keeping the temperature below 45° and chromatographed on two SGF-2000 μm preparative TLC plates using the solvent system: MeOH/Et$_3$N (100+0.2). The major band (R$_f$=0.5) was eluted with MeOH containing sufficient Et$_3$N to keep the pH above 7. A portion of the product, dissolved in 0.1M NaPO$_4$, pH 7.4 gave a UV spectrum with an absorbance maximum of 251 nm with a shoulder at about 275 nm characteristic of 1-substituted inosines. It was also shown to have immunologic activity versus rabbit antiserum (Example 9) to ddI-1-V:BSA (Example 3) by radioimmunoassay using $^3$H-ddI.

EXAMPLE 7 ddI-1-B:BSA Immunogen

Fifty-six milligrams of N-hydroxysulfosuccinimide sodium salt was added to 45 mg (140 μmoles) of ddI-1-BA (Example 6) dissolved in 1ml of DMA and 500 μl of 1M 1,3-dicyclohexycarbodiimide (DCC) in THF was added. The solution was stirred overnight and 50 mg of N-hydroxysuccinimide was added and the mixture again stirred overnight at room temperature. The resulting suspension was added in 50 μl aliquots with vigorous stirring to a chilled (ice-water bath) solution of 60 mg BSA dissolved in 15 ml of 0.15M borax-HCl, pH 8.5. The mixture was incubated 60 hours at 4°, centrifuged, filtered through a 0.8 μm membrane and chromatographed over Sephadex G-25 ®. A 45% yield (biuret) was obtained and an average of 34 moles of hapten were coupled per 66,000 g of protein, assuming a molar extinction coefficient of 10,400 for the hapten at a wavelength of 251 nm.

The same immunization schedule was followed for ddI-1-V:BSA (Example 3) and ddI-1-B:BSA (Example 7).

EXAMPLE 8

4-(2′,3′-dideoxyinosin-1-yl)-butyryl:peroxidase enzyme label (ddI-1-B:HRP)

An active ester was prepared by stirring a mixture of 23 mg (70 μmoles) of ddI-1-BA (Example 6), 28 mg N-hydroxysuccinimide (240 μmoles), 1 ml DMA and 250 μl of 1M DCC in THF overnight at room temperature when 17% conversion was estimated by TLC.

Separate 20 mg aliquots of HRP were dissolved in 2 ml of 0.15M borax-HCl pH 8.5 and treated with 100, 200, 400, or 500 μl of the reaction mixture containing the active ester described above. The sample mixture treated with 500 μl of active ester solution received an additional 2 ml borax buffer. Each reaction mixture was stirred at room temperature, chromatographed over Sephadex G-25 ® (eluting with water) and the colored fractions treated with sodium phosphate to give a final phosphate concentration of 0.1M, pH 7.4.

EXAMPLE 9

Polyclonal Rabbit Antibodies to ddI

The immunogen (1 mg in 1 ml) (ddI-1-V:BSA (Example 3) or ddI-1-B:BSA (Example 7)) was emulsified with an equal volume of Freund's Complete Adjuvant and injected intradermally into each of four female albino rabbits. The process was repeated in two weeks. Two weeks later, monthly subcutaneous booster injections were begun with 0.5 mg (0.5 ml) of the immunogen and 0.5 ml of Freund's Incomplete Adjuvant per animal. The rabbits were bled biweekly by a marginal ear vein technique beginning six weeks after the primary immunization. The blood collected was refrigerated, allowing clots to form, and the supernatant (antiserum) retained. The antiserum from each rabbit was collected and stored at −20° without preservative.

EXAMPLE 10

Radioimmunoassay (RIA) for ddI

The following procedure illustrates the use of various materials of the invention in a preferred RIA method.

(1) 100 μl ddI sample (standard or unknown) was added per test tube in duplicate. An equivalent volume of assay buffer was added to an additional tube labeled NSB (non-specific binding).

(2) 100 μl $^3$H-ddI was added to each tube. Add 100 μl $^3$H-ddI to an additional tube labeled TR (total radioactivity).

(3) 100 μl ddI antibodies (Example 9) were added to each tube except tubes designated NSB and TR. An equivalent volume of assay buffer was added to the NSB tube.

(4) The tubes were incubated at room temperature for 1 hour to allow tracer and standard to competitively bind to ddI antibody.

(5) Sufficient antibody reactive with the ddI antibody to separate the bound from free $^3$H-ddI by immunoprecipitation was added to each tube except the TR tube.

(6) The amount of $^3$H-ddI in the immune precipitate was measured by scintillation counting and reported as the number of disintegrations per minute (dpm).

A plot of the percent dpm bound relative to the bound tracer at a ddI concentration equal to 0 (%B/B$_0$) versus ddI concentration for a set of ddI standards can be used to determine the concentration of ddI in unknowns by interpolation.

Based on this procedure using antibodies (Example 9) produced in rabbits in response to immunization with ddI-1-V:BSA (Example 3), as well as using $^3$H-ddI and ddI standards ranging in concentration from 0.26–10 ng/ml, the data in Table I was obtained.

TABLE I

|  | DPM 1 | DPM 2 | DPM AVG |  |
|---|---|---|---|---|
| TR = | 12156 | 11976 | 12066 | % NSB/TR = 2.12% |
| NSB = | 243 | 268 | 255 | % Bo/TR = 45.04% |
| Conc. (ng/ml) |  |  |  | % B/Bo |
| 0.00 | 5704 | 5445 | 5574 | 100.00% |
| 0.26 | 4986 | 4959 | 4972 | 88.68% |
| 0.64 | 4316 | 4122 | 4219 | 74.52% |
| 1.60 | 3261 | 3215 | 3238 | 56.07% |
| 4.00 | 2016 | 2115 | 2065 | 34.03% |
| 10.00 | 1214 | 1134 | 1174 | 17.27% |

TR = Total Radioactivity
NSB = Non-Specific Binding
B = Bound dpm
Bo = Bound dpm for 0 concentration

EXAMPLE 11

Enzyme Immunoassay (EIA) for ddI

The following procedure illustrates the use of various materials of the invention in a preferred EIA method.

(1) 100 μl ddI sample (standard or unknown) was added per test tube. An equivalent volume of assay buffer was added to an additional tube labeled NSB (non-specific binding).

(2) 100 μl ddI-1-B:HRP (Example 8) was added to each tube. Add 50 μl ddI-1-B:HRP (Example 8) to an additional tube labeled T (total).

(3) 100 μl ddI antibodies (Example 9) were added to each tube except tubes designated NSB and T. An equivalent volume of assay buffer was added to the NSB tube.

(4) The tubes were incubated at room temperature for 2 hours to allow tracer and standard to bind competitively to ddI antibodies (Example 9).

(5) Sufficient antibody reactive with the ddI antibody was added to each tube (except T) to separate the bound from free ddI-1-B:HRP (Example 8) by immunoprecipitation.

(6) Hydrogen peroxide (horseradish peroxidase substrate) and o-phenylenediamine (hydrogen donor) was added to all tubes and the peroxidase reaction was allowed to proceed for 30 minutes for adequate color to develop. The peroxidase reaction was stopped with the addition of 1M sulfuric acid and the absorbance (OD) was measured at 490 nm.

A plot of the absorbance versus ddI concentration for a set of ddI standards can be used to determine the concentration of ddI in unknowns by interpolation.

Based on this procedure using antibodies (Example 9), produced in rabbits in response to immunization with ddI-1-V:BSA (Example 3) as well as ddI-1-B:HRP (Example 8) and ddI standards ranging in concentration from 1 pg/ml–40 ng/ml (useful range), the data in Table II was obtained.

TABLE II

| Sample data | TOTAL NSB Conc. (ng/ml) | Absorbance (OD) 2.159 0.124 Net OD |
|---|---|---|
| 1 | 0.0E + 00 | 0.710 |
| 2 | 2.3E − 05 | 0.705 |
| 3 | 2.6E − 04 | 0.696 |
| 4 | 2.8E − 03 | 0.663 |
| 5 | 3.1E − 02 | 0.618 |
| 6 | 3.4E − 01 | 0.421 |
| 7 | 3.8E + 00 | 0.253 |
| 8 | 4.1E + 01 | 0.188 |
| 9 | 4.5E + 02 | 0.120 |
| 10 | 5.0E + 03 | 0.105 |

Although this invention has been described in some detail and by way of various specific examples in order to illustrate the invention, it will be apparent that various equivalents, changes and modifications may be made without departing from the spirit and scope thereof.

What is claimed is:

1. A compound of the formula:

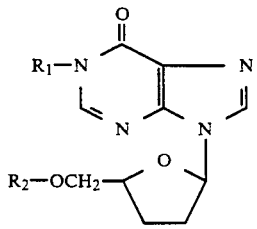

where only one of $R_1$ and $R_2$ is hydrogen and the other of $R_1$ and $R_2$ comprises R-A, R is a linking group, and
 (a) when $R_1$ is hydrogen A is X or Y and
 (b) when $R_2$ is hydrogen A is L, X or Y,
where L is a leaving group, X is an indicator moiety and Y is a carrier.

2. A compound of claim 1 where $R_2$ is hydrogen.
3. A compound of claim 2 where A is Y.
4. A compound of claim 3 where Y is a polyamino acid having a molecular weight of at least about 5,000, a carbohydrate or a liposome.
5. A compound of claim 4 where the polyamino acid is an albumin, a hemocyanin, an enzyme or a globulin.
6. A compound of claim 5 where the albumin is bovine serum albumin.
7. A compound of claim 5 where the hemocyanin is keyhole limpet hemocyanin.
8. A compound of claim 2 where A is X.
9. A compound of claim 8 where X is a fluorescent indicator moiety.

10. A compound of claim 9 where the fluorescent indicator moiety is 5-dimethylaminonaphthalene-1-sulfonyl, rhodamine or fluorescein.
11. A compound of claim 8 where X is a radioactive indicator moiety.
12. A compound of claim 8 where X is an enzyme indicator moiety.
13. A compound of claim 12 where the enzyme indicator moiety is glucose-6-phosphate dehydrogenase, horseradish peroxidase, alkaline phosphatase, glucose oxidase or urease.
14. A compound of claim 8 where X is a phosphorescent indicator moiety, a chemiluminescent indicator moiety, or a multivalent antigen moiety.
15. A compound of claim 14 where the multivalent antigen moiety is latex, erythrocyte, apoferritin, or serum protein.
16. A compound of claim 1 where $R_1$ is hydrogen.
17. A compound of claim 16 where A is X.
18. A compound of claim 17 where X is a fluorescent indicator moiety.
19. A compound of claim 16 where A is Y.
20. A compound of any of claims 2 or 16 where R is —$(CH_2)_m$—NH—, where m is 1-8, copolymerized with protein.
21. A compound of claim 20 where the protein is copolymerized by means of glutaraldehyde.
22. An antibody prepared in response to a compound of the formula:

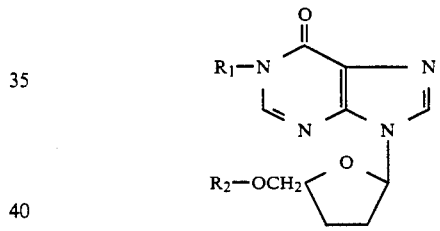

where one of $R_1$ and $R_2$ is hydrogen and the other of $R_1$ and $R_2$ comprises R-Y, R is a linking group, and Y is a carrier.

23. A method for determining ddI in a sample comprising intermixing with said sample a tracer represented by the formula:

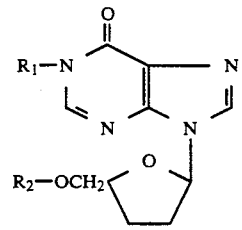

where one of $R_1$ and $R_2$ is hydrogen and the other of $R_1$ and $R_2$ comprises R-X, R is a linking group and X is an indicator moiety, and an antibody capable of specifically recognizing ddI and said tracer, and then determining the amount of tracer bound to antibody as a measure of the amount of ddI in the sample by a suitable assay technique.

24. A method of claim 23 where the indicator moiety is a fluorescent indicator moiety.

25. A method of claim 24 where the fluorescent indicator moiety is fluorescein.

26. A method of any one of claims 23, 24 or 25, where the assay technique is a fluorescence polarization technique.

27. A method of claim 23 where the indicator moiety is an enzyme indicator moiety.

28. A method of claim 27 where the enzyme indicator moiety is horseradish peroxidase, alkaline phosphatase, glucose-6-phosphate dehydrogenase, glucose oxidase or urease.

29. A method of claim 23 where the assay technique is an enzyme technique.

30. A method for determining ddI in a sample comprising intermixing with said sample a tracer of claim 10 and an antibody of claim 22 and then determining the amount of tracer bound to antibody by a fluorescence polarization technique as a measure of the amount of ddI in the sample.

31. A diagnostic kit having component parts adapted to be used together to determine the concentration of ddI in a biological fluid comprising:
 (a) an antibody of claim 22, and
 (b) an indicator moiety of any one of claims 8-15 or 17-18 capable of reacting with said antibody.

32. A diagnostic kit of claim 31 where $R_2$ is hydrogen and A is X.

33. A diagnostic kit of claim 31 where $R_1$ is hydrogen and A is X.

34. A diagnostic kit of claim 32 where the indicator moiety is a fluorescent indicator moiety.

35. A diagnostic kit of claim 33 where the indicator moiety is a fluorescent indicator moiety.

36. A diagnostic kit of claim 31 where A is X and the indicator moiety is one represented by the structure:

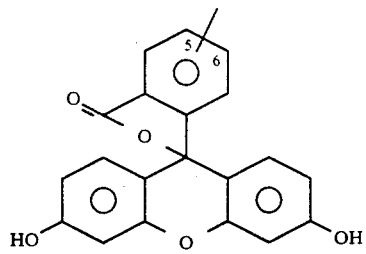

37. A diagnostic kit of claim 31 wherein A is X and the indicator moiety is a fluorescent indicator moiety, further comprising a precipitating agent suitable for reducing non-specific background fluorescence due to materials present in the sample to be analyzed.

38. A compound of any one of claims 16-19 where $R_2$ is succindioyl.

39. A compound of the formula:

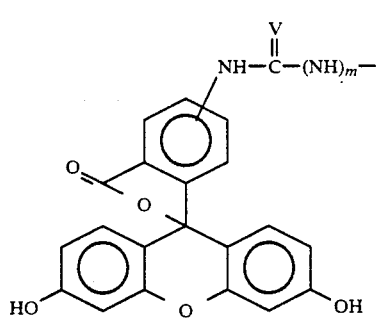

where V is oxygen or sulfur; m is 0 or 1; n is 0 though 8; p is 0 or 1; q is 0 or 1; and r is 1 through 8; except that if m and p are both 1 then n cannot be 1.

40. A compound of the formula:

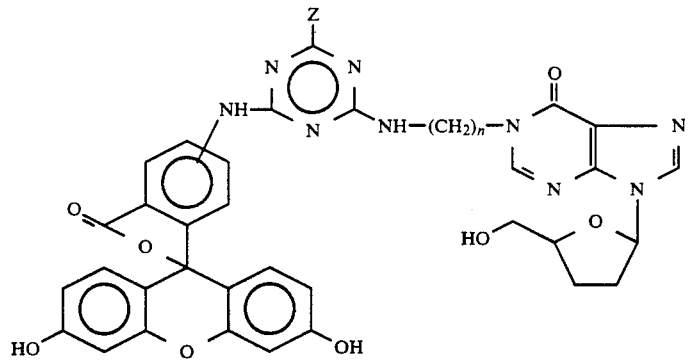

where n is 1-8 and Z is chloro or methoxy.

41. A hybridoma cell line produced by the method comprising:
 a) immunizing an animal with a compound of any of claims 3-7 or 19,
 (b) recovering lymphocytes from said immunized animal,
 (c) fusing said recovered lymphocytes with a myeloma cell line to produce hybridomas, and
 (d) recovering hybridomas that produce antibodies that bind ddI.

42. Monoclonal antibody capable of binding ddI produced by hybridoma cell lines formed by fusion of cells from a mouse myeloma cell line and spleen cells from a mouse previously immunized with a ddI derivative of any of claims 3-7 or 19.

43. An antibody capable of binding ddI prepared in response to a compound of claim 22 wherein Y is bovine serum albumin.

44. An antibody capable of binding ddI prepared in response to a compound of claim 22 where Y is keyhole limpet hemocyanin.

45. A compound of any one of claims 16-19 where $R_2$ is glutardioyl.

46. A compound of claim 2 where A is L.

47. A compound of claim 46 where L is hydrogen, hydroxy, halo, sulfonyloxy, phthalimido, or a group having 1-8 carbon atoms, wherein said group is alkyl, alkoxy, acyl, carbobenzoxy or succinimidoxy.

48. A compound of claim 47 where the group is alkoxy having 1-2 carbon atoms.

* * * * *